United States Patent
Schultz et al.

(10) Patent No.: US 10,758,302 B2
(45) Date of Patent: Sep. 1, 2020

(54) IRRIGATED ABLATION CATHETER WITH SENSOR ARRAY

(71) Applicant: Biosense Webster (Israel) Ltd., Yokneam (IL)

(72) Inventors: Jeffrey Schultz, Chino, CA (US); Kelvin Chuu, Hermosa Beach, CA (US); Daniele Ghidoli, Laguna Hills, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 659 days.

(21) Appl. No.: 14/538,562

(22) Filed: Nov. 11, 2014

(65) Prior Publication Data

US 2016/0128765 A1 May 12, 2016

(51) Int. Cl.
 *A61B 18/14* (2006.01)
 *A61B 18/00* (2006.01)
 (Continued)

(52) U.S. Cl.
 CPC .............. *A61B 18/1492* (2013.01); *A61B 2017/00084* (2013.01); *A61B 2018/00029* (2013.01); *A61B 2018/00065* (2013.01); *A61B 2018/00357* (2013.01); *A61B 2018/00577* (2013.01); *A61B 2018/00648* (2013.01); *A61B 2018/00702* (2013.01); *A61B 2018/00744* (2013.01); *A61B 2018/00797* (2013.01); *A61B 2018/00839* (2013.01); *A61B 2018/00875* (2013.01);
 (Continued)

(58) Field of Classification Search
 CPC ........... A61B 2018/00029; A61B 2018/00065; A61B 2018/00357; A61B 2018/00577
 See application file for complete search history.

(56) References Cited

U.S. PATENT DOCUMENTS

| 5,391,199 A | 2/1995 | Ben-Haim |
| 5,860,951 A * | 1/1999 | Eggers ............... A61B 18/1206 604/510 |

(Continued)

FOREIGN PATENT DOCUMENTS

| CN | 102641153 A | 8/2012 |
| CN | 103181819 A | 7/2013 |

(Continued)

OTHER PUBLICATIONS

European Search Report for European Patent Application No. 15194119.2; dated Feb. 24, 2016.

*Primary Examiner* — Michael F Peffley
*Assistant Examiner* — Bo Ouyang

(57) ABSTRACT

Systems and methods are disclosed for providing and using an irrigated ablation catheter. The catheter may include a distal shell electrode having irrigation apertures. A sensor array formed on a flexible substrate conforms to an inner surface of the electrode and an insert disposed within the interior space engages the sensor array to position sensors of the sensor array in desired locations relative to the electrode. A support seals the proximal end of the electrode and engages the insert. The plurality of sensors may be used to measure electrical and thermal characteristics surrounding the electrode and may help assess contact between the electrode and tissue and/or determine movement of the electrode during ablation.

18 Claims, 5 Drawing Sheets

(51) Int. Cl.
*A61B 17/00* (2006.01)
*A61B 90/00* (2016.01)
*A61M 25/01* (2006.01)

(52) U.S. Cl.
CPC ... *A61B 2090/065* (2016.02); *A61B 2218/002* (2013.01); *A61M 25/0147* (2013.01)

(56) References Cited

U.S. PATENT DOCUMENTS

| | | |
|---|---|---|
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 8,357,152 B2 | 1/2013 | Govari et al. |
| 9,050,105 B2 | 6/2015 | Govari et al. |
| 2002/0006545 A1 | 1/2002 | Marukawa et al. |
| 2003/0120150 A1 | 6/2003 | Govari |
| 2004/0068178 A1 | 4/2004 | Govari |
| 2008/0161797 A1* | 7/2008 | Wang ................ A61B 18/1492 606/41 |
| 2010/0298826 A1* | 11/2010 | Leo ........................ A61B 5/103 606/41 |
| 2010/0331658 A1 | 12/2010 | Isaac et al. |
| 2011/0184406 A1* | 7/2011 | Selkee ................ A61B 5/6885 606/41 |
| 2011/0224573 A1 | 9/2011 | Bar-Tal et al. |
| 2013/0123775 A1* | 5/2013 | Grunewald ........ A61B 18/1492 606/41 |
| 2014/0276052 A1 | 9/2014 | Rankin |

FOREIGN PATENT DOCUMENTS

| | | |
|---|---|---|
| CN | 103860255 A | 6/2014 |
| EP | 2742891 A1 | 6/2014 |
| JP | 2010259810 A | 11/2010 |
| JP | 2012505041 A | 3/2012 |
| JP | 2012531967 A | 12/2012 |
| JP | 2013052241 A | 3/2013 |
| WO | 96/05768 | 2/1996 |
| WO | 2014/072879 A2 | 5/2014 |
| WO | WO2014/072879 A2 | 5/2014 |
| WO | WO-2014072879 A2 * | 5/2014 ............. A61B 8/445 |

* cited by examiner

IRRIGATED ABLATION CATHETER WITH SENSOR ARRAY

FIELD OF THE PRESENT DISCLOSURE

This disclosure relates generally to methods and devices for percutaneous medical treatment, and specifically to catheters, in particular, irrigated ablation catheters. More particularly, this disclosure relates to irrigated ablation catheters designs featuring a sensor array for accurate thermal and/or electrical sensing properties while providing reduced interference with irrigation of the ablation electrode.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In such procedures, a reference electrode is typically provided and may be attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue. During this process, heating of the electrode also occurs as a result of conduction from the heated tissue to the electrode itself.

Correspondingly, irrigation of the ablation catheter may provide many benefits including cooling of the electrode and tissue to prevent overheating of tissue that can otherwise cause the formation of char and coagulum and even steam pops. Therefore, an irrigated ablation catheter may include one or more temperature sensors, such as thermocouples, thermistors or the like, to assess tissue temperature during an ablation procedure for avoiding such adverse occurrences. It is desirable that the sensed temperature accurately reflects the real temperature of the tissue and not merely tissue temperature which has been biased by the cooling irrigation fluid from the catheter. Moreover, an irrigated ablation catheter may alternatively or in addition include electrical sensors for multiple purposes, including measuring impedance to help determine lesion size, depth and transmurality, performing mapping functions or assessing tissue contact with the RF electrode.

Further, the distal end of an irrigated ablation catheter is subject to significant spatial and design constraints. Since the catheter gains access via an intravascular route, the overall diameter is limited and must be sufficiently flexible to navigate the tortuous anatomy. There must also be an irrigation conduit system to supply the cooling fluid. The distal end also needs to accommodate the above noted RF electrode, temperature sensors and electrical sensors, and the associated electrical connections as well as other functional components that may be included, such as contact force sensor systems, safety wires or other structures.

Accordingly, it would be desirable to provide an irrigated ablation catheter that has one or more temperature and/or electrical sensors positioned at the distal end. It is also desirable to reduce interference between such elements and the irrigation system. For example, it would be desirable to provide the sensors in a manner that increases the surface area of the RF electrode exposed to the irrigation fluid. Likewise, it would be desirable to provide the sensors in a manner that reduces the effect of the irrigation fluid on the measurements. Still further, it would be desirable to facilitate transmission of data from the sensors. As will be described in the following materials, this disclosure satisfies these and other needs.

SUMMARY

The present disclosure is directed to a catheter having an elongated body, an electrode mounted at a distal end of the elongated body, wherein the electrode is configured as a shell defining an interior space, a plurality of irrigation apertures formed in the shell and communicating with the interior space, a sensor array disposed within the interior space, comprising a flexible substrate, a plurality of sensors secured to the substrate and a plurality of traces on the substrate coupled to the sensors, wherein the sensor array conforms to an inner surface of the electrode and each sensor extends into a corresponding plurality of orifices in the shell of the electrode, an insert disposed within the interior space configured to engage the sensor array such that each sensor is positioned in a desired location relative to the electrode and a support which forms a fluid tight seal with a proximal end of the electrode and engages a proximal end of the insert to stabilize the insert against rotational motion.

In one aspect, the sensor array may have at least one wing carrying at least one of the sensors. Further, the insert may have at least one arm configured to engage a corresponding wing of the sensor array. Still further, the at least one wing may have a plurality of sensors. The arm may also have an interior lumen to isolate wires coupled to the sensors.

In one aspect, the sensor array may have a plurality of wings and the insert may have a corresponding plurality of arms. The insert may include at least one passageway between the plurality of arms to allow circulation of irrigation fluid within the interior space. Further, the support may engage a proximal portion of the plurality of arms of the insert.

In one aspect, the sensor array may include a sensor controller. The sensor controller may digitize signals received from the sensors before transmitting them along the elongated body.

In one aspect, at least some of the plurality of sensors may be temperature sensors. In another aspect, at least some of the plurality of sensors may be electrical sensors. Alternatively or in addition, at least one of the plurality of sensors may be a combined temperature and electrical sensor.

This disclosure is also directed to a method for the ablation of a portion of tissue of a patient by an operator. One suitable method includes inserting a catheter into the patient, wherein the catheter has an elongated body, an electrode mounted at a distal end of the elongated body, wherein the electrode is configured as a shell defining an interior space, a plurality of irrigation apertures formed in the shell and communicating with the interior space, a sensor array disposed within the interior space, comprising a flexible substrate, a plurality of sensors secured to the substrate and a plurality of traces on the substrate coupled to the sensors, wherein the sensor array conforms to an inner surface of the electrode and each sensor extends into a corresponding plurality of orifices in the shell of the electrode, such that each sensor, an insert disposed within the interior space configured to engage the sensor array such that each sensor is positioned in a desired location relative to the electrode and a support which forms a fluid tight seal with a proximal end of the electrode and engages a proximal end of the insert to stabilize the insert against rotational motion, then connecting the catheter to a system controller capable of receiving signals from the plurality of sensors and delivering power to the electrode and subsequently controlling the power to the electrode to ablate tissue.

In one aspect, power to the electrode to ablate tissue may be controlled based at least in part on measurements from the plurality of sensors.

In one aspect, irrigation fluid may be delivered to the interior space based at least in part on measurements from the plurality of sensors.

In one aspect, contact of the electrode with tissue may be distinguished from contact of the electrode with blood based at least in part on measurements from the plurality of sensors.

In one aspect, a degree of contact of the electrode with tissue may be estimated based at least in part on measurements from the plurality of sensors.

In one aspect, movement of the electrode during ablation may be determined based at least in part on measurements from the plurality of sensors.

In one aspect, signals received from the sensors may be digitized before transmitting them along the elongated body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
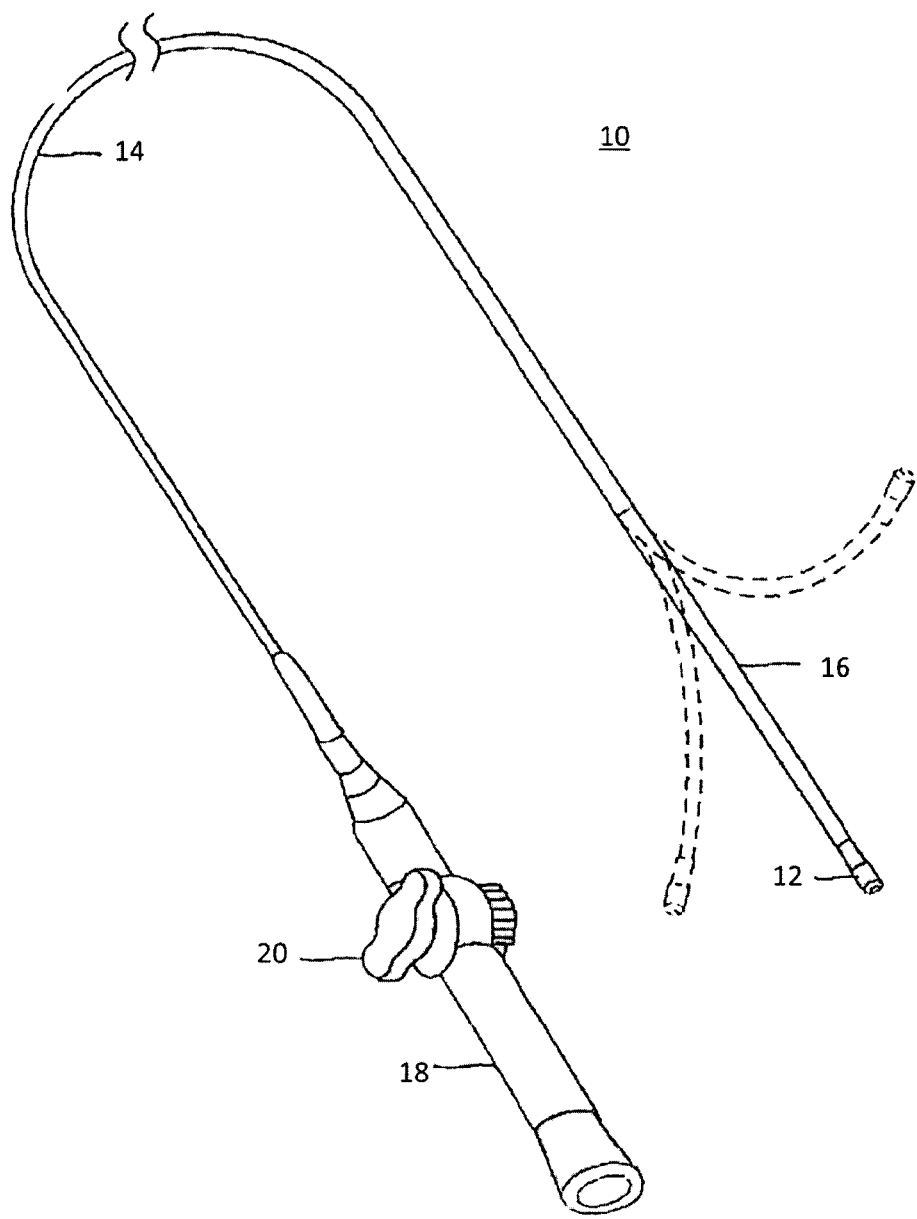
FIG. 1 is a perspective view of a catheter in accordance with an embodiment of the present invention.

As illustrated in FIG. 1, the present disclosure includes irrigated ablation catheter 10 with a distal tip section that includes electrode 12 adapted for contact with target tissue. Catheter 10 according to the disclosed embodiments comprises an elongated body that includes an insertion shaft or catheter body 14 having a longitudinal axis, and an intermediate section 16 distal of the catheter body that optionally may be uni- or bi-directionally deflectable off-axis from the catheter body as indicated. Proximal of catheter body 14 is control handle 18 that allows an operator to maneuver the catheter, including by deflecting intermediate section 14 when a steerable embodiment is employed. For example, control handle 18 may include deflection knob 20 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500, 167, and 6,522,933 and U.S. patent application Ser. No. 12/960,286, filed Dec. 3, 2010, the entire disclosures of which are incorporated herein by reference.

Catheter body 14 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 14 so that, when the control handle 20 is rotated, the intermediate section 16 will rotate in a corresponding manner. Depending upon the intended use, the outer diameter of catheter body 14 may be approximately 8 french, and in some embodiments, may be 7 french. Likewise the thickness of the outer wall of catheter body 14 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm. The length of the intermediate section 16 may correspond to a relatively small portion of the useful length, such as from about 3.5 cm to about 10 cm, and in some embodiments, from about 5 cm to about 6.5 cm.

Figure 2:
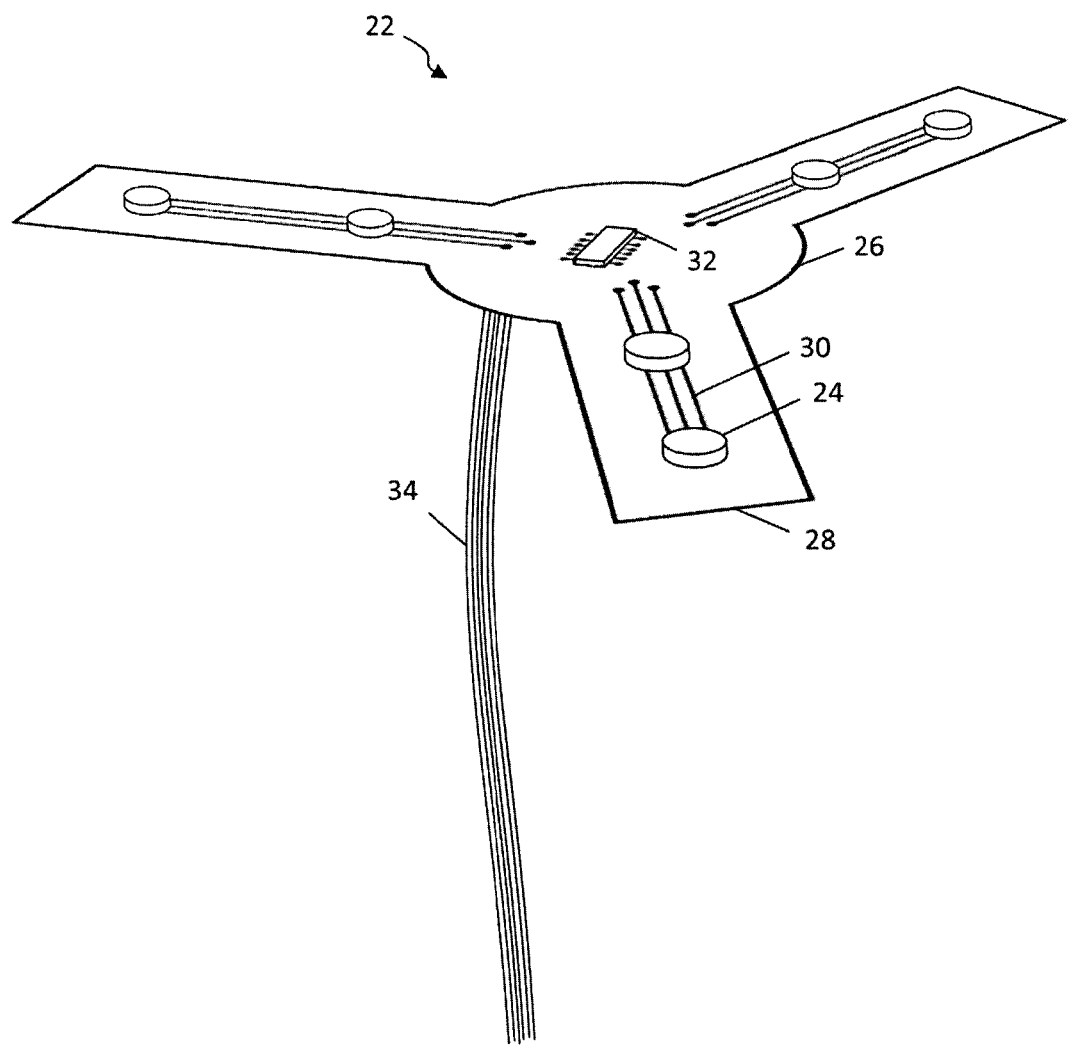
FIG. 2 is a perspective view of a sensor array for use within a distal electrode of the catheter of FIG. 1 in accordance with an embodiment of the present invention.

According to the techniques of this disclosure, electrode 12 may include sensor array 22, generally having features as depicted in FIG. 2. As shown, sensor array 22 may include a plurality of sensors 24 disposed on flexible substrate 26 that may be nominally planar but may bend or deflect to conform to the inner surface of electrode 12 when disposed within it. Substrate 26 may feature one or more wings 28, such as the three depicted in this embodiment, to facilitate sensor array 22 in assuming a shape dictated by the inner surface of electrode 12. Further, each wing may accommodate one or more sensors 24 (e.g. two as shown). Sensors 24 may be any combination of temperature sensors, e.g., thermistor, thermocouple, fluoroptic probe, and the like, or electrical sensors, e.g., micro-electrodes. Each sensor 24 may be potted, over molded, or otherwise encapsulated or sealed to enable contact with blood, tissue, and/or irrigation fluid.

Substrate 26 may be formed using techniques for constructing flexible circuits, or "flex circuits," known in the art. Substrate 26 may be any suitable flexible polymer, such as polyester, polyimide, polyethylene napthalate (PEN), polyetherimide (PEI), fluropolymers (FEP), PEEK or the like, including copolymers. Generally, substrate 26 may be provided with conductive leads and traces as desired using metallic foil and photolithography or equivalent techniques, although suitable patterns of conductive tape may be laminated between layers of polymer or electro-deposition methods may also be used. For example, traces 30 on substrate 26 may be used to electrically couple sensors 24.

In this embodiment, sensors 24 may provide output over traces 30 to sensor controller 32, which may be configured to perform desired operations on data from the sensors. In one aspect, this may include providing analog to digital conversion of the sensor measurements. Sensor controller 32 may also include a suitable interface to transmit sensor data from sensor array 22 through the body 14 of catheter 10. Further, sensor controller 32 may provide pre-processing of data from sensors 24 as desired, including filtering, amplification or other suitable signal manipulations. Sensor controller 32 may be configured as a digital signal processor (DSP), an application specific integrated circuit (ASICs, an application specific instruction set processors (ASIP), a field programmable gate arrays (FPGA), or other equivalent integrated or discrete logic circuitry, or combinations thereof. Sensor controller 32 may use any suitable interface to communicate sensor data from sensors 24, such as an inter-integrated circuit (I2C) bus, a universal asynchronous receiver/transmitter (UART) serial bus, a serial digital input output (SDIO) bus, a serial peripheral interface (SPI), a universal serial bus (USB), a peripheral component interconnect (PCI) bus, or other equivalent interface. As will be appreciated, the digitization and interface capabilities provided by sensor controller 32 may reduce the number of wires needed to transmit signals from sensors 24 through catheter 10, effectively reducing spatial constraints and allowing greater flexibility in accommodating the other elements of catheter 10. In some embodiment, signals from sensors 24 may be carried over a single wire, depending on the interface used.

In other embodiments, traces 30 may terminate in pads to allow connection of lead wires routed through catheter body 14 that may be used to conduct signals from sensors 24.

Whether first processed by sensor controller 32 or delivered directly, signals from sensors 24 may be carried over cable 34, which is routed through catheter body 14 to the proximal end for suitable connection as described below.

Figure 3:
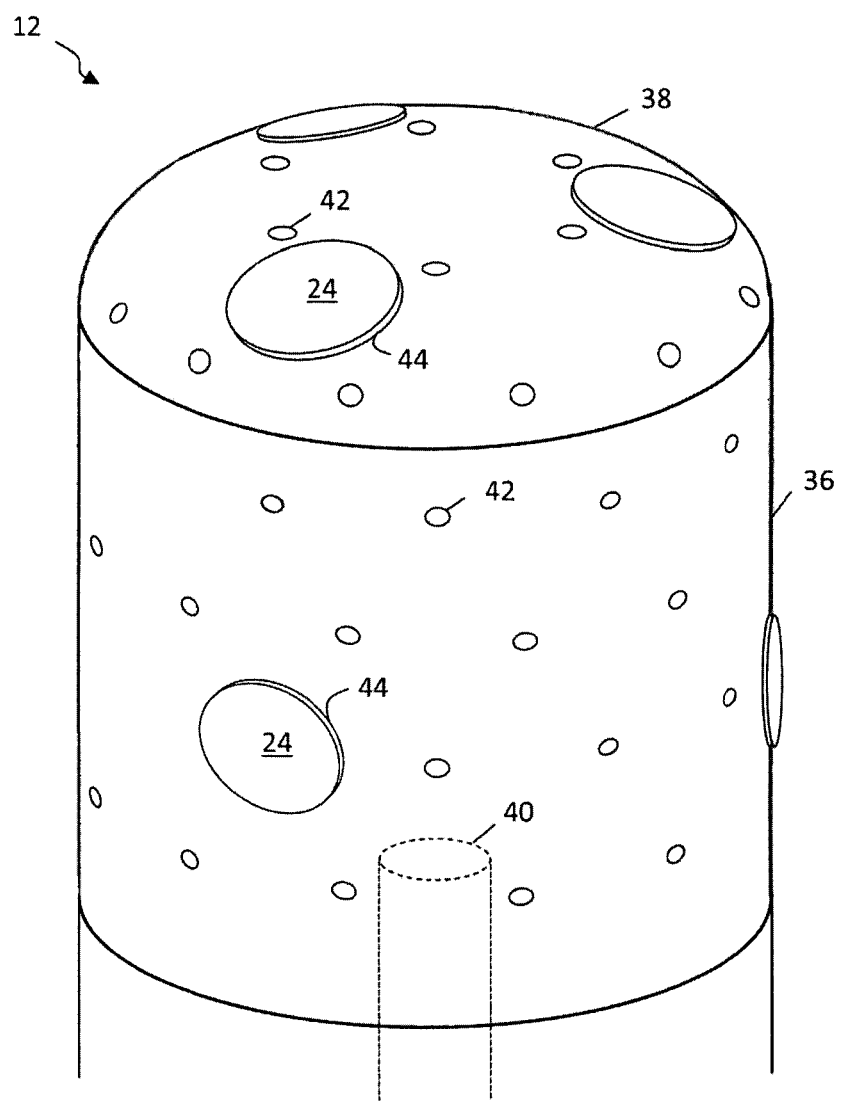
FIG. 3 is a perspective view of the distal electrode in accordance with an embodiment of the present invention.

Details regarding the configuration of electrode 12 and sensors 24 are shown in FIG. 3. Electrode 12 is configured as an elongated, generally cylindrical portion 36 and an atraumatic dome-shaped portion 38 at the distal end. The shell of electrode 12 defines an interior cavity that is in fluid communication with lumen 40 (shown in phantom) extending the length of catheter body 14 to supply irrigation fluid. A plurality of irrigation apertures 42 are distributed substantially evenly across the surface of electrode 12, through which fluid entering and filling the cavity may exit to outside of the electrode 12, to provide cooling of electrode 12 and the environment adjacent electrode 12 as desired. The shell of electrode 12 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Sensor array 22 is disposed within electrode 12 with wings 28 bending to conform to the inner surface of electrode 12 and position the plurality of sensors 24 to align with sensor orifices 44 formed in electrode 12. The number of sensors 24 may depend on the intended use of catheter 10 or other design choices. In this embodiment, three proximal sensors are radially spaced by approximately 120 degrees about cylindrical portion 36 and three distal sensors are radially spaced by approximately 120 degrees about dome-shaped portion 38, reflecting the three wing design of sensor array 22. In other embodiments, other suitable configurations may be employed, such as by varying the number of wings 28 and/or the number of sensors 24 on each wing. The depth of sensors 24 in conjunction with the thickness of electrode 12 may be adjusted so that sensors 24 either extend beyond or to are flush with the outer surface of electrode 12 as desired. For example, sensors 24 may extend from the shell a distance ranging from about 0.05-0.3 mm and in one embodiment may extend between about 0.07 and 0.13 mm.

Figure 4:
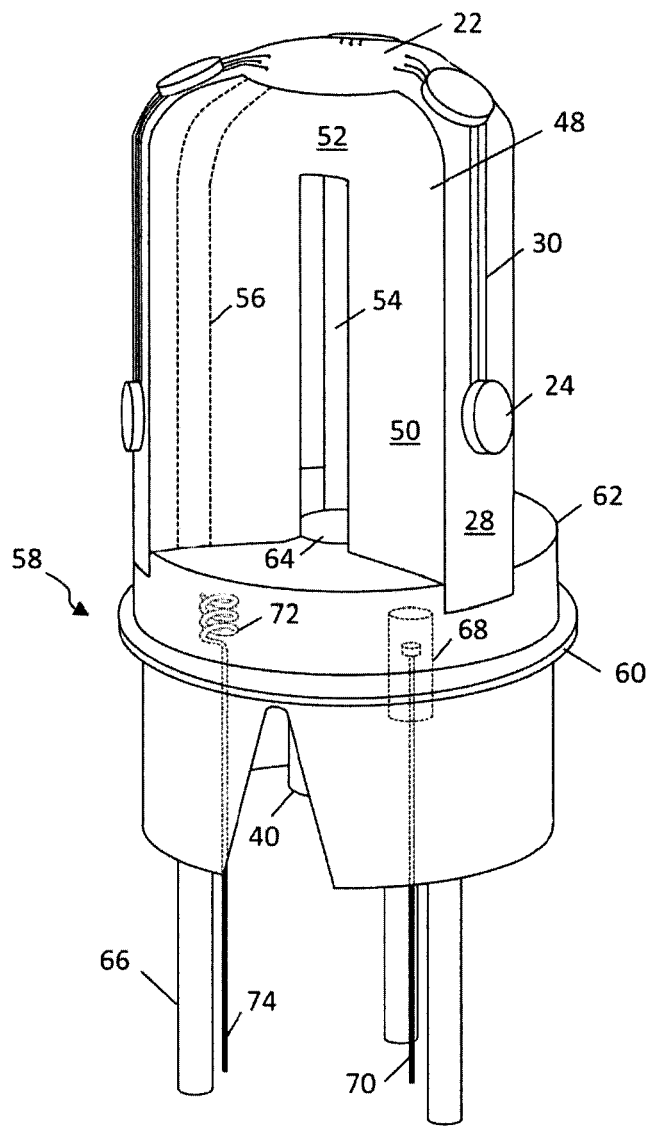
FIG. 4 is a schematic view of the sensor array and insert in accordance with an embodiment of the present invention.

To further illustrate the placement of sensor array 22 within electrode 12, FIG. 4 depicts the distal end of catheter 10 with electrode 12 removed. Insert 48 is configured to stabilize sensor array 22 after it is positioned within electrode 12 by engaging the surface of sensor array 22 opposing the surface with sensors 24. As such, insert 48 may include three longitudinally extending arms 50, corresponding to the wings 28 of sensor array 22. Arms 50 are connected at distal crown portion 52, and together, these elements define an outer surface that fits closely within electrode 12 to sandwich sensor array 22. In one aspect, insert 48 engages a substantial portion of the opposing surface of sensor array 24 such as 50 percent or more. For example, in one embodiment, approximately 75 percent and in another embodiment 90 percent of the opposing surface is engaged. In the depicted embodiment, substantially all the opposing surface of sensor array 24 is engaged. Passageways 54 between arms 50 facilitate circulation and even distribution of irrigation fluid supplied through lumen 40. Insert 48 may have one or more interior lumens 56 (one shown in phantom) configured to route wires or leads, such as cable 34 (not shown in this view) extending from sensor array 22. The configuration of insert 48 may be adapted as necessary to complement the chosen design of sensor array 22. In general, insert 48 may have an outer surface that is coextensive with the footprint of sensor array 22 when flexed into contact with the inner surface of electrode 12. Insert 28 may be formed from any suitable material having appropriate electrical and thermal insulating properties, such as PEEK.

As will be appreciated, the configuration of insert 48 helps insulate sensors 24 from irrigation fluid circulating throughout the interior of electrode 12. Accordingly, a more accurate measurement of tissue and environmental temperature may be obtained by reducing biasing. In another aspect, insert 48 also serves to electrically insulate sensors 24 to allow more accurate measurement. Similarly, any wires and/or leads are also thermally and electrically insulated, as well as being sealed against corrosion from the irrigation fluid. Further, individual wires may be isolated from each other by any suitable technique, such as by employing a suitable electrically nonconductive and non-thermally insulative material to fill interior lumen 56. As desired, sensor array 24 may employ scallops, cut outs or other similar features to reduce the amount of the inner surface of electrode 12 that is covered by sensor array 24. Accordingly, by increasing the inner surface area of electrode 12 that is exposed to irrigation fluid, the techniques of this disclosure provide more efficient control over the temperature of electrode 12 during ablation.

In another aspect of this disclosure, insert 48 is stabilized within electrode 12 by support 58, which includes a disc-shaped base 60 and a distally projecting key 62. Base 60 may have a diameter corresponding to the inner diameter of electrode 12 and may be secured in any suitable manner, such as by welding. Key 62 is configured to mate with the proximal portions of arms 50, to stabilize insert 48 against axial rotation and possible displacement of sensors 24. Support 58 may provide a fluid tight seal with electrode 12 while routing leads and wires associated with electrode 12 and sensors 24 and irrigation fluid from lumens extending through catheter body 14. For example, central conduit 64 may be in communication with lumen 40 to conduct irrigation fluid for circulation within the interior of electrode 12 and eventual exit through apertures 42. Through-holes in support 58 may align with the interior of arms 50 to accommodate passage of wires to sensor array 22. Guide tubes 66 may route and protect the wires and leads as they extend through catheter body 14 to support 58. Guide tubes 66 may be formed of any suitable material that is fluid-tight, electrically-nonconductive, thermally-insulating, and sufficiently flexible, e.g., polyimide, to form a thin-walled tubing. Support 58 may be formed of any suitable electrically- and thermally-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

As desired, support 58 may also include blind hole 68 (shown in phantom) to serve as an anchor point for safety wire 70 to facilitate retrieval of the electrode assembly or other distal portions of catheter 10 should they become detached during a procedure. Safety wire 70 may be formed from Vectran™ or other suitable materials. Support 58 may also include RF coil 72, fed by lead 74, to energize electrode 12. In other embodiments, support 58 may be configured to accommodate electromagnetic position sensors that may be used in conjunction with a mapping system to aid visualization of the placement of the distal end of catheter 10 within a patient's anatomy and/or a force or contact sensing system. Details regarding such aspects may be found in U.S. patent application Ser. Nos. 11/868,733 and 13/424,783, both of which are incorporated herein by reference in their entirety.

According to the techniques of this disclosure, sensor array 22 may be used to provide catheter 10 with multiple sensors 24. In one aspect, each sensor may measure temperature and electrical characteristics as described above, to allow for direct monitoring of micro ECG signals and/or micro impedance values. As will be appreciated, use of either, or both, ECG and impedance provide the ability to determine the contacting tissue at the location of each sensor and help distinguish between blood and tissue. This information may be utilized to confirm sufficient tissue coupling prior to delivery of RF ablation. This may be employed alternatively or in addition to the use of contact force sensors. Additionally, monitoring of electrical feedback from the plurality of sensors 24 of sensor array 22 distributed across electrode 12 may allow for estimation of a degree of contact between electrode 12 and tissue. For example, the measurements may be used to estimate the percentage of the surface of electrode 12 that is coupled with tissue. In turn, this may be used to better characterize the efficacy of RF delivery by determining what portion of the energy is delivered to tissue as compared to the surrounding blood.

In another aspect, sensor array 22 according to the techniques of this disclosure may provide improved temperature response to facilitate determination of catheter movement. As will be appreciated, dragging catheter 10 along tissue may result in frequent rise and fall of temperature response from tissue contacting sensors 24. For example, ablations at a first position followed by movement to a new location may correspond to temperature increase during RF delivery followed by an abrupt decrease in interface temperature at the time of movement, and then by a temperature increase when RF delivery occurs at the new location. Consequently, the ability to quickly detect catheter movement using sensed temperature in this manner may allow for lesion assessment algorithms to "reset" mid ablation and account for detected movement.

In comparison to conventional RF ablation catheters, the techniques of this disclosure represent notable benefits. Prior to ablation, tissue and blood are at a similar temperature preventing use of temperature sensors from being utilized to determine contact, or more specifically areas of an electrode in contact. Contact force catheters are capable of demonstrating contact with tissue but do not provide an indication as to how much of the electrode is in contact with tissue. Further, such conventional contact force technologies may provide information regarding the contact with tissue. However, they do not provide an indication of movement during RF delivery by using the temperature sensing described above. The use of sensor array 22 to accommodate multiple sensors 24 provides sufficient resolution and response time to indicate ablation site movement.

Figure 5:
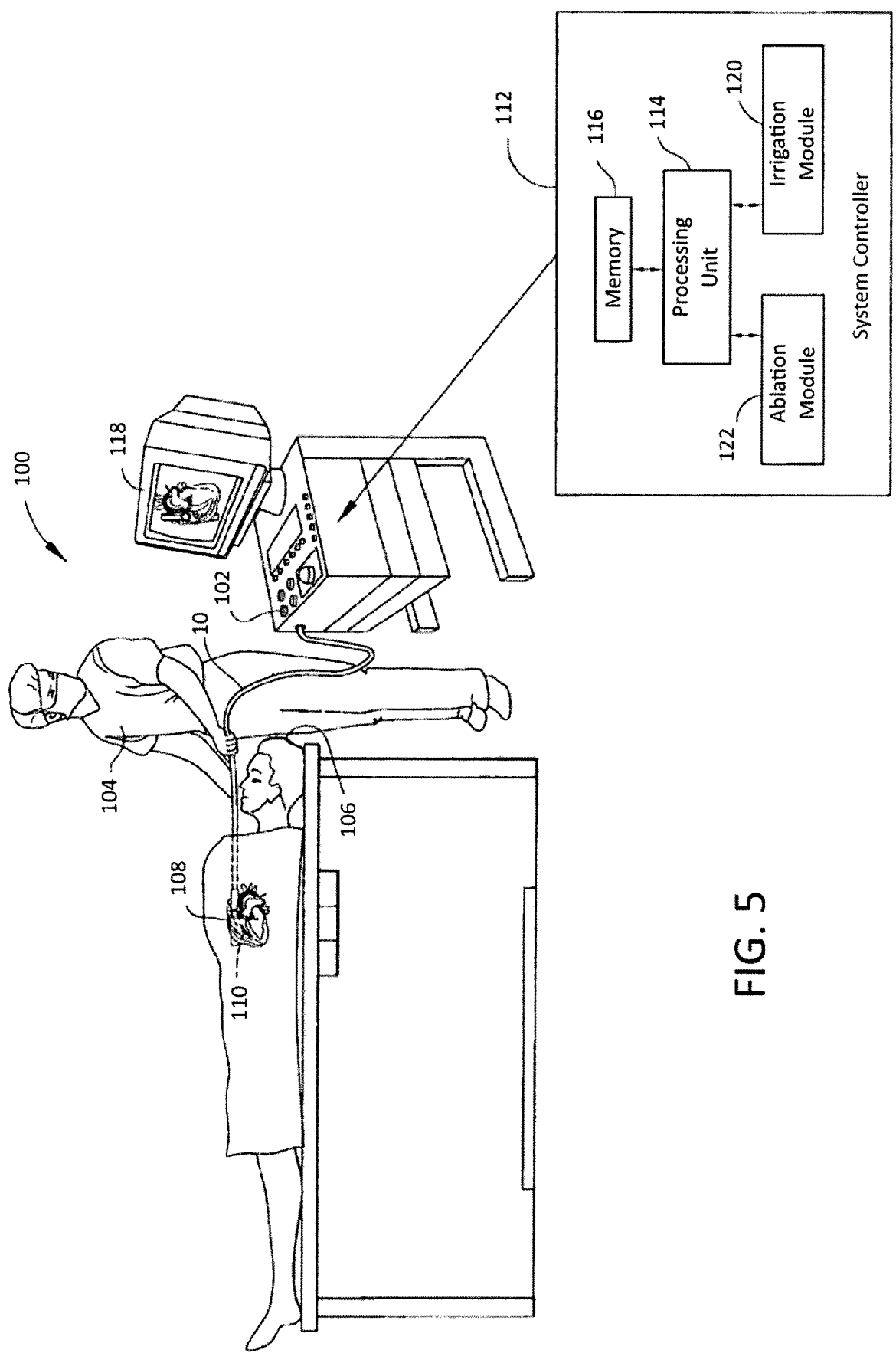
FIG. 5 is a schematic view of an ablation system in accordance with an embodiment of the present invention.

Use of catheter 10 in an ablation procedure may follow techniques known to those of skill in the art. FIG. 5 is a schematic, pictorial illustration of a system 100 for renal and/or cardiac catheterization and ablation, in accordance with an embodiment of the present invention. System 100 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 and a control and/or ablation console 102. An operator 104, such as a cardiologist, electrophysiologist or interventional radiologist, inserts ablation catheter 10 into and through the body of a patient 106, such as through a femoral or radial access approach, so that a distal end of catheter 10, in particular, electrode 12, engages tissue at a desired location or locations, such as a chamber of heart 108 of patient 106. Catheter 10 is typically connected by a suitable connector at its proximal end to console 102. Console 102 comprises a RF generator 108, which supplies high-frequency electrical energy via the catheter for ablating tissue 110 at the locations engaged by electrode 12.

Console 102 may also use magnetic position sensing to determine position coordinates of the distal end of catheter 10 inside the body of the patient 106. For this purpose, a driver circuit in console 102 drives field generators to generate magnetic fields within the body of patient 106. Typically, the field generators comprise coils, which are placed below the patient's torso at known positions external to the patient. These coils generate magnetic fields in a predefined working volume that contains the area of interest. A magnetic field sensor within distal end of catheter 10 generates electrical signals in response to these magnetic fields. A signal processor in console 102 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 102 may include system controller 112, comprising a processing unit 114 communicating with a memory 116, wherein is stored software for operation of system 100. Controller 112 may be an industry standard personal computer comprising a general purpose computer processing unit. However, in some embodiments, at least some of the functions of the controller are performed using custom designed application specific integrated circuits (ASICs) or a field programmable gate array (FPGA). Controller 112 is typically operated by the operator 104 using suitable input peripherals and a graphic user interface (GUI) 118 which enable the operator to set parameters of the system 100. GUI 118 typically also displays results of the procedure to the operator. The software in memory 114 may be downloaded to the controller in electronic form, over a network, for example. Alternatively or additionally, the software may be provided on non-transitory tangible media such as optical, magnetic or electronic storage media. In some embodiments, one or more position sensors may send signals to console 102 to provide an indication of the pressure on electrode 12. Signals from cable 34 may be provided to system controller 112 to obtain measurements from sensors 24. Such signals may be used to provide impedance and/or ECG readings at the location corresponding to sensor 24. Similarly, such signals may be used to provide a temperature reading at the location of sensor 24.

Typically, during an ablation, heat is generated by the RF energy in the tissue of the patient to effect the ablation and some of this heat is reflected to the electrode 12 causing coagulation at and around the electrode. System 100 irrigates this region through irrigation apertures 42 and the rate of flow of irrigation is controlled by irrigation module 120 and the power (RF energy) sent to electrode 12 is controlled by ablation module 122. As noted above, system controller 112 may use electrical and thermal characteristics measured by the plurality of sensors 24 to characterize aspects of the ablation process. For example, measurements from sensors 24 may be used to determine the contacting tissue at the location of each sensor and help distinguish between blood and tissue. Further, the percentage of the surface of electrode 12 that is coupled with tissue may be estimated. As another example, measurements from sensors 24 may help determine movement of electrode 12 during an ablation. Still further, information from sensors 24 may be used to determine the lesion size and depth. Details regarding this aspect may be found in U.S. patent application Ser. No. 13/113,159, entitled "Monitoring Tissue Temperature Using an Irrigated Catheter" the teachings of which is hereby incorporated by reference in its entirety. As yet another example, sensors 24 may also provide intracardiac electrocardiograms to system controller 112, to be used for determining when the tissue site being ablated is no longer conducting arrhythmogenic currents.

Described herein are certain exemplary embodiments. However, one skilled in the art that pertains to the present embodiments will understand that the principles of this disclosure can be extended easily with appropriate modifications to other applications.

What is claimed is:

1. A catheter, comprising:
    an elongated body;
    an electrode mounted at a distal end of the elongated body, wherein the electrode is configured as a shell defining an interior space;
    a plurality of irrigation apertures formed in the shell and communicating with the interior space;
    a sensor array disposed within the interior space, comprising:
        a flexible substrate;
        a plurality of sensors secured to the substrate;
        at least one nominally planar, and substantially rectangular wing carrying at least one of the sensors; and
        a plurality of traces on the substrate coupled to the sensors;
    wherein the sensor array conforms to an inner surface of the electrode and each sensor extends into a corresponding plurality of orifices in the shell of the electrode;
    an insert disposed within the interior space configured to engage the sensor array such that each sensor is positioned in a desired location relative to the electrode, the insert having at least one arm configured to engage a corresponding wing of the sensor array, the at least one arm being sized to complement the corresponding wing of the sensor array; and
    a support which forms a fluid tight seal with a proximal end of the electrode and engages a proximal end of the insert to stabilize the insert against rotational motion.

2. The catheter of claim 1, wherein the at least one wing has a plurality of sensors.

3. The catheter of claim 1, wherein the at least one arm has an interior lumen to isolate wires coupled to the sensors.

4. The catheter of claim 1, wherein the sensor array comprises a plurality of wings and the insert comprises a corresponding plurality of arms.

5. The catheter of claim 4, further comprising at least one passageway between the plurality of arms to allow circulation of irrigation fluid within the interior space.

6. The catheter of claim 5, wherein the support engages a proximal portion of the plurality of arms of the insert.

7. The catheter of claim 1, wherein the sensor array further comprises a sensor controller.

8. The catheter of claim 7, wherein the sensor controller digitizes signals received from the sensors before transmitting them along the elongated body.

9. The catheter of claim 1, wherein at least some of the plurality of sensors are temperature sensors.

10. The catheter of claim 1, wherein at least some of the plurality of sensors are electrical sensors.

11. The catheter of claim 1, wherein at least one of the plurality of sensors is a combined temperature and electrical sensor.

12. A method for the ablation of a portion of tissue of a patient by an operator comprising:
   inserting a catheter into the patient, wherein the catheter comprises:
      an elongated body;
      an electrode mounted at a distal end of the elongated body, wherein the electrode is configured as a shell defining an interior space;
      a plurality of irrigation apertures formed in the shell and communicating with the interior space;
      a sensor array disposed within the interior space, comprising:
         a flexible substrate;
         a plurality of sensors secured to the substrate;
         at least one nominally planar, and substantially rectangular wing carrying at least one of the sensors; and
         a plurality of traces on the substrate coupled to the sensors;
         wherein the sensor array conforms to an inner surface of the electrode and each sensor extends into a corresponding plurality of orifices in the shell of the electrode;
      an insert disposed within the interior space configured to engage the sensor array such that each sensor is positioned in a desired location relative to the electrode, the insert having at least one arm configured to engage a corresponding wing of the sensor array, the at least one arm being sized to complement the corresponding wing of the sensor array; and
      a support which forms a fluid tight seal with a proximal end of the electrode and engages a proximal end of the insert to stabilize the insert against rotational motion;
   connecting the catheter to a system controller capable of receiving signals from the plurality of sensors and delivering power to the electrode; and
   controlling the power to the electrode to ablate tissue.

13. The method of claim 12, wherein controlling the power to the electrode to ablate tissue is based at least in part on measurements from the plurality of sensors.

14. The method of claim 12, further comprising delivering irrigation fluid to the interior space based at least in part on measurements from the plurality of sensors.

15. The method of claim 12, further comprising distinguishing contact of the electrode with tissue from contact of the electrode with blood based at least in part on measurements from the plurality of sensors.

16. The method of claim 12, further comprising estimating a degree of contact of the electrode with tissue based at least in part on measurements from the plurality of sensors.

17. The method of claim 12, further comprising determining movement of the electrode during ablation based at least in part on measurements from the plurality of sensors.

18. The method of claim 12, further comprising digitizing signals received from the sensors before transmitting them along the elongated body.

* * * * *